(12) United States Patent
Chuu et al.

(10) Patent No.: US 9,173,914 B2
(45) Date of Patent: Nov. 3, 2015

(54) EXTRACTION TECHNOLOGY OF XIAO-YAO-DRINK

(71) Applicants: MESOPHASE TECHNOLOGIES, INC, Tainan (TW); Mei-Wen Kao, Tainan (TW)

(72) Inventors: Jiunn-Jye Chuu, New Taipei (TW); Mei-Wen Kao, Tainan (TW)

(73) Assignees: Mesophase Technologies, Inc., Tainan (TW); Mei-Wen Kao, Tainan (TW)

( * ) Notice: Subject to any disclaimer, the term of this patent is extended or adjusted under 35 U.S.C. 154(b) by 393 days.

(21) Appl. No.: 13/726,707

(22) Filed: Dec. 26, 2012

(65) Prior Publication Data

US 2014/0120130 A1    May 1, 2014

(30) Foreign Application Priority Data

Nov. 1, 2012    (TW) .............................. 101140623 A (51) Int. Cl.
| | |
|---|---|
| *A61K 36/00* | (2006.01) |
| *A61K 36/268* | (2006.01) |
| *A61K 36/236* | (2006.01) |
| *A61K 36/53* | (2006.01) |
| *A61K 36/284* | (2006.01) |
| *A61K 36/076* | (2006.01) |
| *A61K 36/185* | (2006.01) |
| *A61K 36/232* | (2006.01) |
| *A61K 36/484* | (2006.01) |
| *A61K 36/534* | (2006.01) |
| *A61K 36/65* | (2006.01) |
| *A61K 36/9068* | (2006.01) |

(52) U.S. Cl.
CPC ............. *A61K 36/185* (2013.01); *A61K 36/076* (2013.01); *A61K 36/232* (2013.01); *A61K 36/284* (2013.01); *A61K 36/484* (2013.01); *A61K 36/534* (2013.01); *A61K 36/65* (2013.01); *A61K 36/9068* (2013.01); *A61K 2236/00* (2013.01)

(58) Field of Classification Search
None
See application file for complete search history.

(56) References Cited

FOREIGN PATENT DOCUMENTS

CN           101766801 A    *    7/2010

* cited by examiner

*Primary Examiner* — Qiuwen Mi
(74) *Attorney, Agent, or Firm* — Alan D. Kamrath; Kamrath IP Lawfirm, P.A.

(57) ABSTRACT

An extraction technology of a Xiao-yao-drink includes a medicine preparing step of preparing herbal medicines, a pulverizing step of pulverizing the herbal medicines to produce medicinal solid particles, a liquid extracting step of adding the medicinal solid particles into an extraction liquid to dissolve the medicinal solid particles in the extraction liquid, an ultrasonic extraction step of impacting the medicinal solid particles in the extraction liquid by concentrated ultrasonic waves to crush the medicinal solid particles into medicinal molecules, and a centrifugal filtering step of filtering the medicinal molecules from the extraction liquid by a strainer cloth to produce a medicinal extract which constructs a Xiao-yao-drink product. Thus, the extraction technology uses an ultrasonic extraction procedure to crush the medicinal solid particles into medicinal molecules by concentrated ultrasonic waves to efficiently increase the active component of the herbal medicine.

5 Claims, 7 Drawing Sheets

EXTRACTION TECHNOLOGY OF XIAO-YAO-DRINK

BACKGROUND OF THE INVENTION

1. Field of the Invention

The present invention relates to an extraction technology of a Chinese traditional medicine and, more particularly, to an extraction technology of a Xiao-yao-drink (XYD).

2. Description of the Related Art

The Xiao-yao-san (XYS) is a Chinese medicinal formula for treating anxiety and depression. A conventional extraction technology of the XYS comprises a water extraction process that is performed at a high temperature. For the conventional water extraction process, one kilogram (1 kg) of the XYS powder was suspended in ten liters (10 L) of double distilled water and extracted with hot water by boiling twice for one point five hour (1.5 h) each. Then, the residues were filtered to obtain the XYS. However, the Chinese herb medicine compositions are very complex, and the conventional extraction technology for extracting effective components of the XYS have many disadvantages, such as long cycle processes, insufficient extraction rates and residual organic solvents. In addition, the conventional extraction technology of the XYS is operated at a high temperature, thereby wasting the energy.

BRIEF SUMMARY OF THE INVENTION

In accordance with the present invention, there is provided an extraction technology of a Xiao-yao-drink, comprising a medicine preparing step of preparing a plurality of herbal medicines, a pulverizing step of pulverizing the herbal medicines to produce medicinal solid particles, a liquid extracting step of adding the medicinal solid particles into an extraction liquid to dissolve the medicinal solid particles in the extraction liquid, an ultrasonic extraction step of impacting the medicinal solid particles in the extraction liquid by concentrated ultrasonic waves to crush the medicinal solid particles in the extraction liquid into medicinal molecules, and a centrifugal filtering step of filtering the medicinal molecules from the extraction liquid by a strainer cloth to produce a medicinal extract which constructs a Xiao-yao-drink product. In the medicine preparing step, the herbal medicines includes *Mentha arvensis*, *Glycyrrhiza uralensis*, *Zingiber officinale*, *Angelica sinensis*, *Vatica mangachapoi Blanco*, *Wolfiporia cocos*, *Atractylodes macrocephala Koidz*, and *Paeonia lactiflora*.

Preferably, all of the steps of the extraction technology of the Xiao-yao-drink are kept at a temperature ranged between 25° C. and 35° C.

Preferably, in the liquid extracting step, the extraction liquid includes water or alcohol.

Preferably, the mixture proportion of the medicinal solid particles to the extraction liquid is about 1:3. Alternatively, the mixture proportion of the medicinal solid particles to the extraction liquid is about 1:5. Alternatively, the mixture proportion of the medicinal solid particles to the extraction liquid is about 1:10.

Preferably, in the ultrasonic extraction step 4, the concentrated ultrasonic waves are provided by an ultrasonic equipment with a volume of one hundred liters (100 L).

Preferably, the ultrasonic extraction step has a cycle time of about one hour.

Preferably, in the centrifugal filtering step, the strainer cloth has two hundred and fifty (250) meshes.

The primary objective of the present invention is to provide an extraction technology of a Xiao-yao-drink having a better antidepressant effect.

According to the primary advantage of the present invention, the extraction technology of the Xiao-yao-drink uses an ultrasonic extraction procedure to crush the medicinal solid particles into medicinal molecules by concentrated ultrasonic waves to efficiently increase the active component of the herbal medicine, thereby greatly enhancing the antidepressant effect.

According to another advantage of the present invention, all of the procedures of the extraction technology of the Xiao-yao-drink are operated and kept at a temperature ranged between 25° C. and 35° C., without having to increase or decrease the temperature of operation, thereby achieving an energy-saving function.

Further benefits and advantages of the present invention will become apparent after a careful reading of the detailed description with appropriate reference to the accompanying drawings.

DETAILED DESCRIPTION OF THE INVENTION

Figure 1:
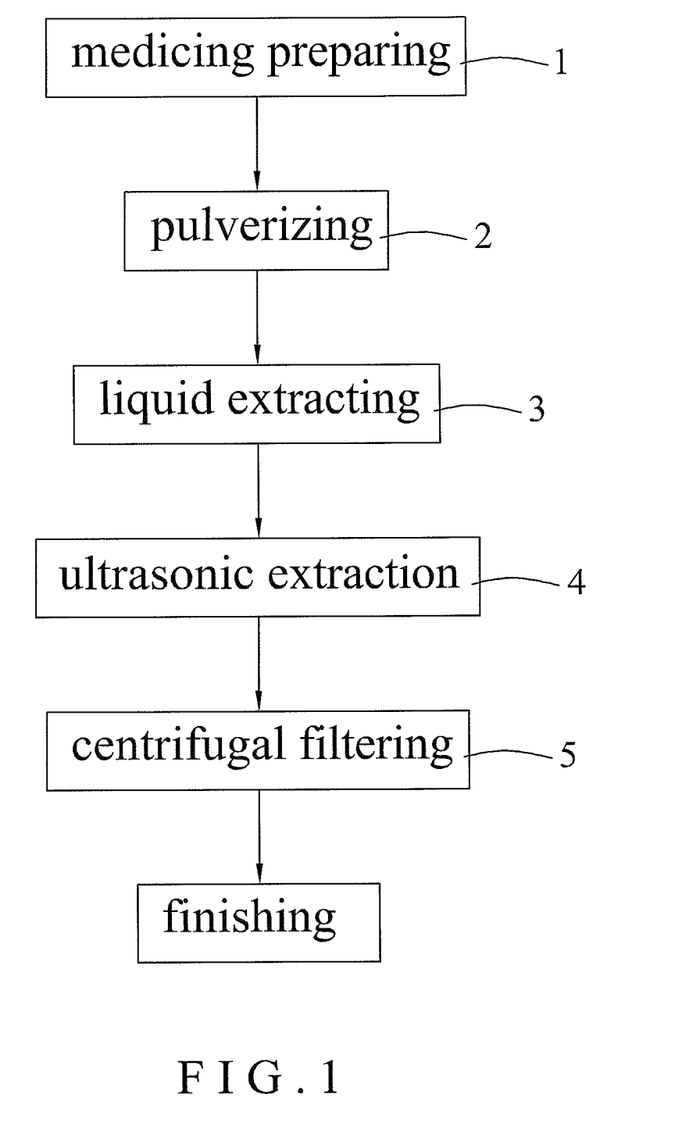
FIG. 1 is a flow chart of an extraction technology of a Xiao-yao-drink in accordance with the preferred embodiment of the present invention.

Referring to the drawings and initially to FIG. 1, an extraction technology of a Xiao-yao-drink in accordance with the preferred embodiment of the present invention comprises a medicine preparing step 1 of preparing a plurality of herbal medicines, a pulverizing step 2 of pulverizing the herbal medicines to produce medicinal solid particles, a liquid extracting step 3 of adding the medicinal solid particles into an extraction liquid to dissolve the medicinal solid particles in the extraction liquid, an ultrasonic extraction step 4 of impacting the medicinal solid particles in the extraction liquid by concentrated ultrasonic waves to crush the medicinal solid particles in the extraction liquid into medicinal molecules, and a centrifugal filtering step 5 of filtering the medicinal molecules from the extraction liquid by a strainer cloth to produce a medicinal extract which constructs a Xiao-yao-drink product. The Xiao-yao-drink product can be further processed and packaged.

In the medicine preparing step 1, the herbal medicines includes *Mentha arvensis*, *Glycyrrhiza uralensis*, *Zingiber* officinale, *Angelica sinensis, Vatica mangachapoi Blanco, Wolfiporia cocos, Atractylodes macrocephala Koidz*, and *Paeonia lactiflora*. In addition, the herbal medicines may include other medicines with different effects. In the pulverizing step 2, the herbal medicines are placed in and pulverized by a pulverizer to produce the medicinal solid particles. In the liquid extracting step 3, the extraction liquid includes water or alcohol. Preferably, the mixture proportion of the medicinal solid particles to the extraction liquid is about 1:3, that is, the medicinal solid particles per one gram is mixed with the extraction liquid per three grams. Alternatively, the mixture proportion of the medicinal solid particles to the extraction liquid is about 1:5, that is, the medicinal solid particles per one gram is mixed with the extraction liquid per five grams. Alternatively, the mixture proportion of the medicinal solid particles to the extraction liquid is about 1:10, that is, the medicinal solid particles per one gram is mixed with the extraction liquid per ten grams. In the ultrasonic extraction step 4, the concentrated ultrasonic waves are provided by an ultrasonic equipment with a volume of one hundred liters (100 L). In addition, the ultrasonic extraction step 4 has a cycle time of about one hour. In the centrifugal filtering step 5, the strainer cloth has two hundred and fifty (250) meshes. All of the steps of the extraction technology of the Xiao-yao-drink are kept at a temperature ranged between 25° C. and 35° C.

In practice, the complete procedures of the extraction technology of the Xiao-yao-drink in accordance with the preferred embodiment of the present invention are described as follows. First of all, the herbal medicines are selected and prepared, which includes *Mentha arvensis, Glycyrrhiza uralensis, Zingiber officinale, Angelica sinensis, Vatica mangachapoi Blanco, Wolfiporia cocos, Atractylodes macrocephala Koidz*, and *Paeonia lactiflora*. Then, the herbal medicines are placed in the pulverizer to proceed a pulverizing process so that the herbal medicines are pulverized to produce the medicinal solid particles. Then, the medicinal solid particles are added into the extraction liquid to dissolve in and mix with the extraction liquid. Then, the medicinal solid particles in the extraction liquid are impacted by the concentrated ultrasonic waves of the ultrasonic equipment during a period of time of about one hour so that the medicinal solid particles in the extraction liquid are crushed into medicinal molecules. Then, the medicinal molecules in the extraction liquid are filtered by the strainer cloth to obtain a medicinal extract. Thus, the medicinal extract constructs a Xiao-yao-drink product. All of the above procedures of the extraction technology of the Xiao-yao-drink are kept at a temperature ranged between 25° C. and 35° C.

In experimentation, the Xiao-yao-drink (XYD) in accordance with the preferred embodiment of the present invention proceeded animal experiments including an elevated-plus maze (EPM), a tail suspension test (TST), and a forced swim test (FST), to compare with a conventional Xiao-yao-san (XYS) and a conventional Fluoxetine.

Referring to FIGS. 2-5, the EPM experiment was performed by an equipment which includes two open arms (30×5 cm) and two closed arms (30×5×15 cm) connected by a square (5×5 cm), which were elevated to a height of 50 cm above the floor. A mouse was placed in the equipment to start exploring the maze from the intersection of the open arms and the closed arms of the equipment for a consecutive period of time of about five (5) minutes. The mouse faced the open arms. When the mouse spent more time in the open arms, the mouse was more regular, and when the mouse spent more time in the closed arms, the mouse was more irregular or depressive.

In the drawings, the marking "Control" indicates a normal mouse (control group) that is not fed with any medicine, the marking "Normal" indicates a depressive mouse that is not fed with any medicine, the marking "Fluoxetine" indicates a depressive mouse that is fed with the Fluoxetine (10 mg/kg), the marking "XYS" indicates a depressive mouse that is fed with the XYS (5 g/kg), and the marking "XYD" indicates a depressive mouse that is fed with the XYD (5 g/kg).

Figure 2:
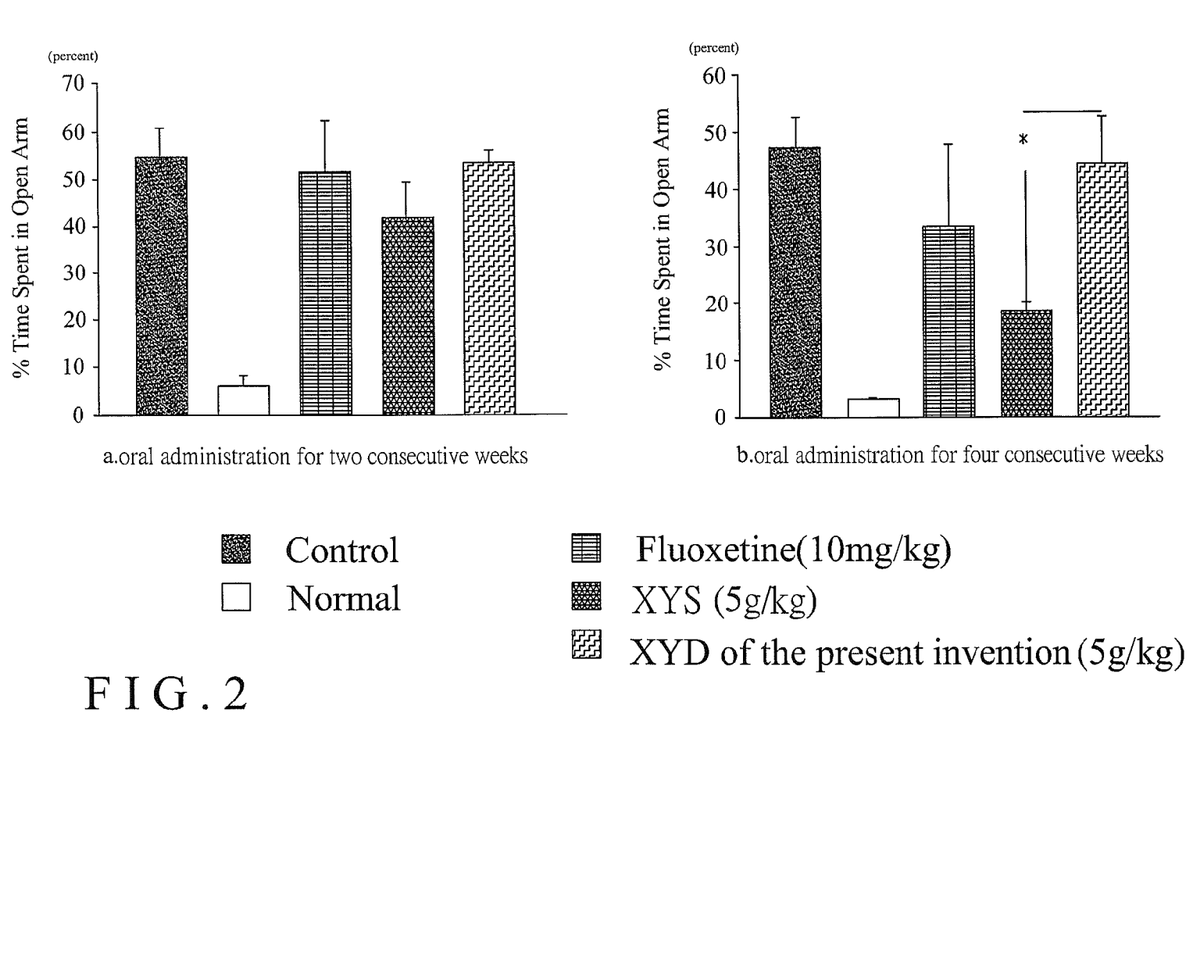
FIG. 2 is a data graph showing the time spent in the open arm when the Xiao-yao-drink of the present invention is performed by an elevated-plus maze (EPM).

As shown in FIG. 2, when the mice were fed during two consecutive weeks and four consecutive weeks, the Fluoxetine, the XYS and the XYD increased the time spent in the open arm after oral administration for two consecutive weeks and four consecutive weeks. An increase in the time spent in the open arm was indicative of an antidepressant effect. In addition, the XYD increased the most time spent in the open arm, compared with the same treatment of the Fluoxetine and the XYS.

Figure 3:
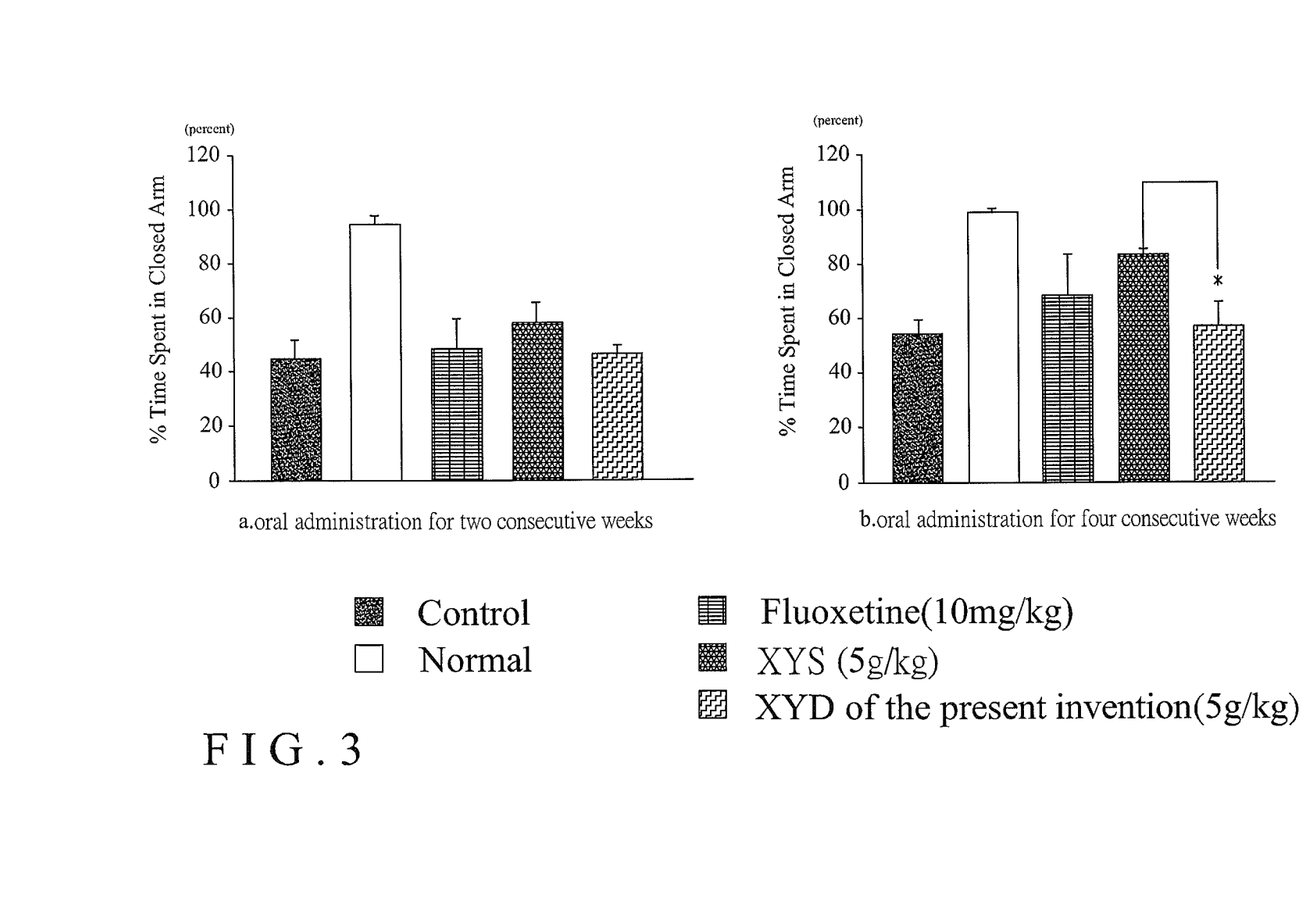
FIG. 3 is a data graph showing the time spent in the closed arm when the Xiao-yao-drink of the present invention is performed by an elevated-plus maze (EPM).

As shown in FIG. 3, when the mice were fed during two consecutive weeks and four consecutive weeks, the Fluoxetine, the XYS and the XYD decreased the time spent in the closed arm after oral administration for two consecutive weeks and four consecutive weeks. A decrease in the time spent in the closed arm was indicative of an antidepressant effect. In addition, the XYD decreased the most time spent in the closed arm, compared with the same treatment of the Fluoxetine and the XYS.

Figure 4:
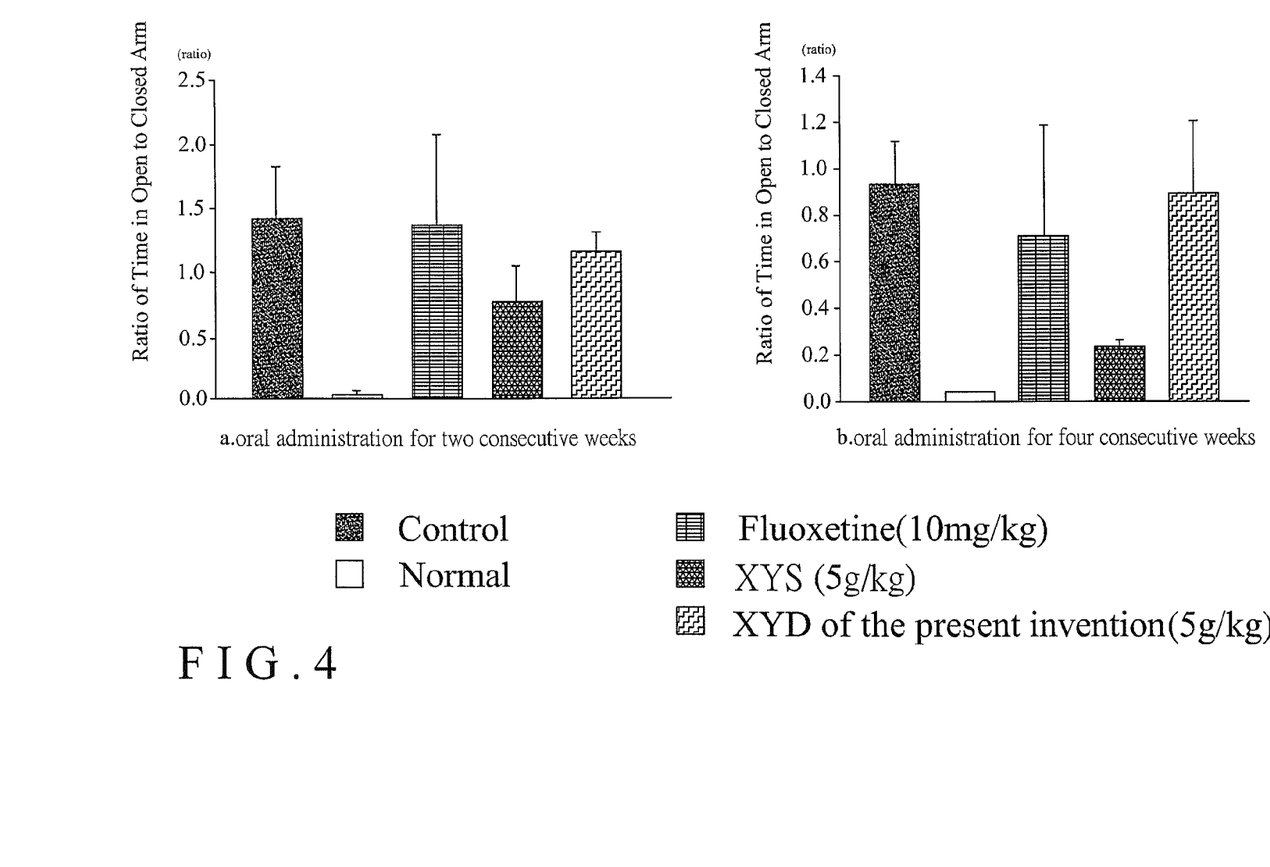
FIG. 4 is a data graph showing the ratio of time in open to closed arm when the Xiao-yao-drink of the present invention is performed by an elevated-plus maze (EPM).

As shown in FIG. 4, when the mice were fed during two consecutive weeks and four consecutive weeks, the Fluoxetine, the XYS and the XYD increased the ratio of time in open to closed arm (the time spent in the open arm/the time spent in the closed arm) after oral administration for two consecutive weeks and four consecutive weeks. It is to be noted that, when the mouse spent more time in the open arms, the mouse was more regular, and when the mouse spent more time in the closed arms, the mouse was more irregular or depressive. Thus, when the ratio of time in open to closed arm is greater, the mouse was more regular, and when the ratio of time in open to closed arm is smaller, the mouse was more irregular or depressive. It is clear in the figure that, the XYD has the greatest ratio of time in open to closed arm after oral administration for four consecutive weeks, compared with the same treatment of the Fluoxetine and the XYS'. Thus, the XYD in accordance with the present invention has the greatest antidepressant effect.

Figure 5:
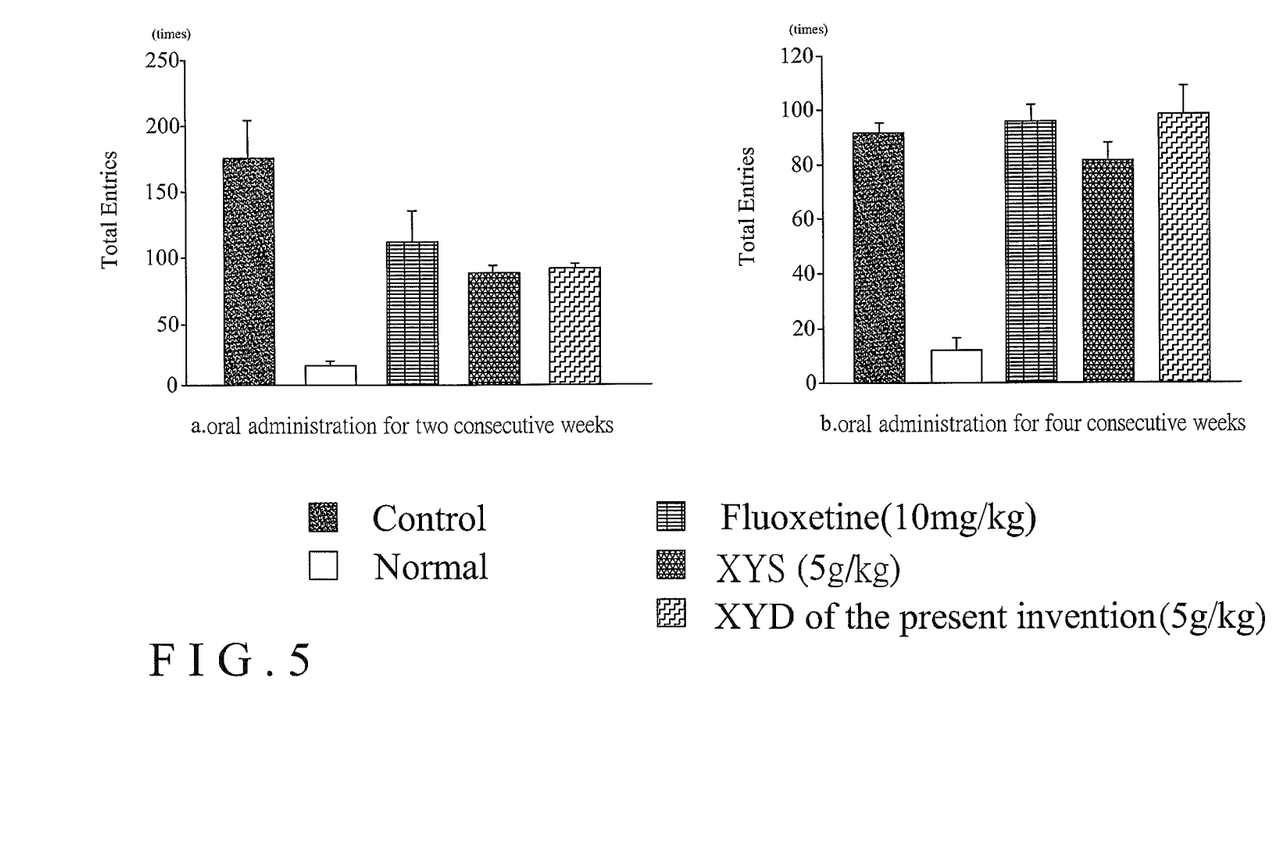
FIG. 5 is a data graph showing the number of total entries when the Xiao-yao-drink of the present invention is performed by an elevated-plus maze (EPM).

As shown in FIG. 5, when the mice were fed during two consecutive weeks and four consecutive weeks, the Fluoxetine, the XYS and the XYD increased the number of total entries to the intersection of the open arm and the closed arm, after oral administration for two consecutive weeks and four consecutive weeks. It is clear in the figure that, the XYD has the greatest number of total entries to the intersection of the open arm and the closed arm after oral administration for four consecutive weeks, compared with the same treatment of the Fluoxetine and the XYS.

Figure 6:
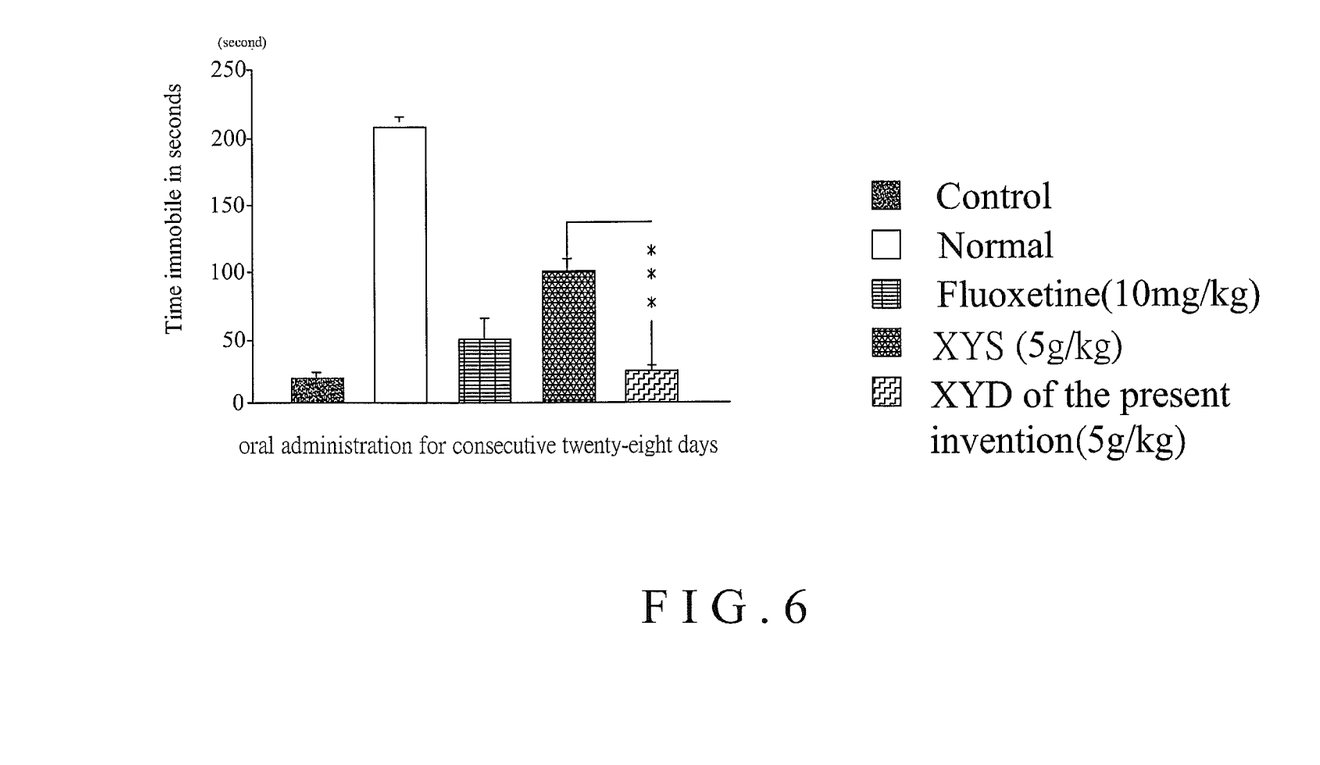
FIG. 6 is a data graph showing the immobility time of the mice when the Xiao-yao-drink of the present invention is performed by a tail suspension test (TST).

Referring to FIG. 6, in the tail suspension test (TST), when the tail of the mouse is hung up, the mouse is suspended in the air. Thus, the mouse will struggle by twisting its body and try to escape. After a period of time (about six minutes in the TST), the mouse will give up due to helplessness and stops moving so that the mouse presents a depressive behavior. In practice, when the mice were fed during consecutive twenty-eight (28) days, the Fluoxetine, the XYS and the XYD decreased the immobility time of the mice after oral administration for consecutive twenty-eight days. A decrease in the duration of immobility was indicative of an antidepressant effect. In addition, the XYD decreased the most immobility time, compared with the same treatment of the Fluoxetine and the XYS. Thus, the XYD in accordance with the present invention has the greatest antidepressant effect.

Figure 7:
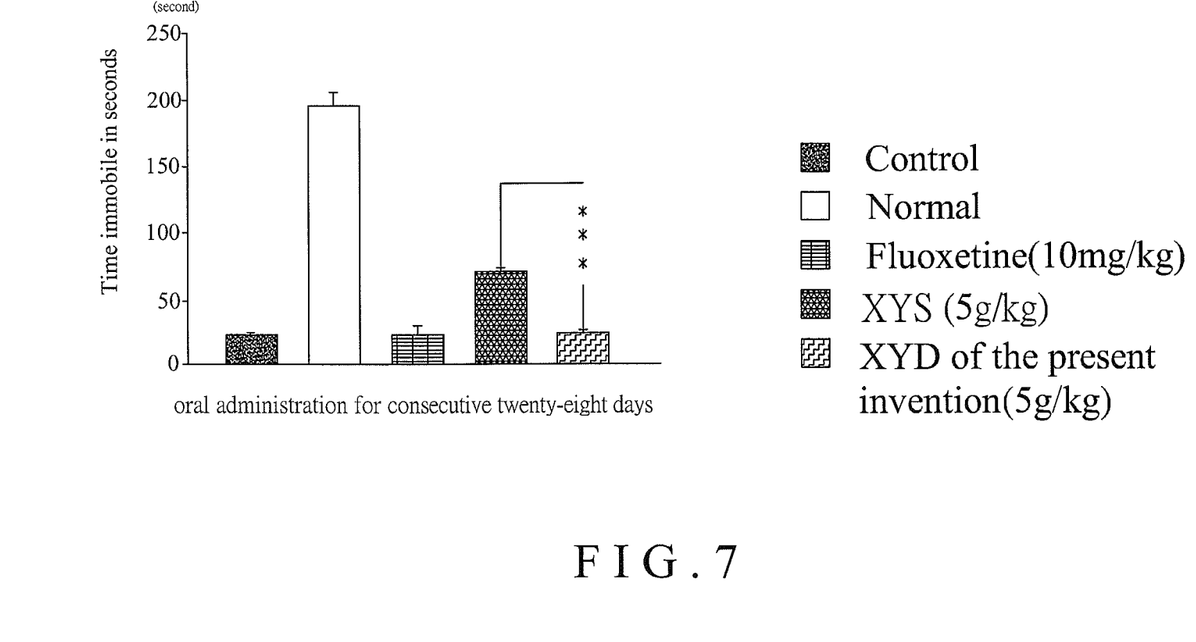
FIG. 7 is a data graph showing the immobility time of the mice when the Xiao-yao-drink of the present invention is performed by a forced swim test (FST).

Referring to FIG. 7, in the forced swim test (FST), individual mice were forced to swim in an open transparent cylindrical container (25 cm height and 10 cm diameter) filled with water at 22-25° C. up to a height of 10 cm. The total duration of immobility was evaluated in a six (6) minute swim session in the FST. The mice were considered immobile when they made only the movements necessary to keep their head above the water so that the mice present a depressive behavior. In practice, when the mice were fed during consecutive twenty-eight (28) days, the Fluoxetine, the XYS and the XYD decreased the immobility time of the mice after oral administration for consecutive twenty-eight days. A decrease in the duration of immobility was indicative of an antidepressant effect. In addition, the XYD decreased the most immobility time, compared with the same treatment of the Fluoxetine and the XYS. Thus, the XYD in accordance with the present invention has the greatest antidepressant effect.

Accordingly, the extraction technology of the Xiao-yao-drink in accordance with the present invention uses an ultrasonic extraction procedure to crush the medicinal solid particles into medicinal molecules by concentrated ultrasonic waves to efficiently increase the active component of the herbal medicine, thereby greatly enhancing the antidepressant effect. In addition, all of the procedures of the extraction technology of the Xiao-yao-drink are operated and kept at a temperature ranged between 25° C. and 35° C., without having to increase or decrease the temperature of operation, thereby achieving an energy-saving function.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. An extraction technology of a Xiao-yao-drink, comprising:
   a medicine preparing step of preparing a plurality of herbal medicines;
   a pulverizing step of pulverizing the herbal medicines to produce medicinal solid particles;
   a liquid extracting step of adding the medicinal solid particles into an extraction liquid which is water to dissolve the medicinal solid particles in the extraction liquid;
   an ultrasonic extraction step of impacting the medicinal solid particles in the extraction liquid by concentrated ultrasonic waves with a volume of one hundred liters (100 L) and with a cycle time of about one hour to crush the medicinal solid particles in the extraction liquid into medicinal molecules; and
   a centrifugal filtering step of filtering the medicinal molecules from the extraction liquid by a strainer cloth to produce a medicinal extract which constructs a Xiao-yao-drink product;
   wherein in the medicine preparing step, the herbal medicines includes *Mentha arvensis, Glycyrrhiza uralensis, Zingiber officinale, Angelica sinensis, Vatica mangachapoi Blanco, Wolfiporia cocos, Atractylodes macrocephala Koidz*, and *Paeonia lactiflora*;
   the ultrasonic extraction step is directly performed after the medicinal solid particles are dissolved in the extraction liquid of water; and
   all of the steps of the extraction technology of the Xiao-yao-drink are kept at a temperature ranged between 25° C. and 35° C.

2. The extraction technology of a Xiao-yao-drink of claim 1, wherein the mixture proportion of the medicinal solid particles to the extraction liquid is about 1:3.

3. The extraction technology of a Xiao-yao-drink of claim 1, wherein the mixture proportion of the medicinal solid particles to the extraction liquid is about 1:5.

4. The extraction technology of a Xiao-yao-drink of claim 1, wherein the mixture proportion of the medicinal solid particles to the extraction liquid is about 1:10.

5. The extraction technology of a Xiao-yao-drink of claim 1, wherein in the centrifugal filtering step, the strainer cloth has two hundred and fifty (250) meshes.

\* \* \* \* \*